(12) United States Patent
Isomura et al.

(10) Patent No.: US 7,921,692 B2
(45) Date of Patent: Apr. 12, 2011

(54) SENSOR

(75) Inventors: Hiroshi Isomura, Aichi (JP); Takaya Yoshikawa, Aichi (JP); Junji Kawai, Aichi (JP); Hisaharu Nishio, Aichi (JP)

(73) Assignee: NGK Spark Plug Co., Ltd., Nagoya, Aichi (JP)

( * ) Notice: Subject to any disclaimer, the term of this patent is extended or adjusted under 35 U.S.C. 154(b) by 466 days.

(21) Appl. No.: 12/132,207

(22) Filed: Jun. 3, 2008

(65) Prior Publication Data

US 2008/0302171 A1    Dec. 11, 2008

(30) Foreign Application Priority Data

Jun. 5, 2007  (JP) ................. 2007-149448
Apr. 17, 2008  (JP) ................. 2008-107530

(51) Int. Cl.
*G01N 7/06* (2006.01)
(52) U.S. Cl. ............................................. 73/23.31
(58) Field of Classification Search ........... 73/23.2, 73/23.31, 31.05; 204/424, 428, 431
See application file for complete search history.

(56) References Cited

U.S. PATENT DOCUMENTS

| 4,362,605 | A | * | 12/1982 | Bozon et al. ............. 205/784 |
| 4,507,192 | A | * | 3/1985 | Ebizawa et al. ........... 204/428 |
| 4,655,892 | A | * | 4/1987 | Satta et al. ............. 204/192.15 |
| 4,741,816 | A | * | 5/1988 | Nishio et al. ............. 204/425 |
| 5,880,353 | A | * | 3/1999 | Graser et al. ............. 73/23.2 |
| 6,360,581 | B1 |   | 3/2002 | Murase et al. |
| 7,559,224 | B2 | * | 7/2009 | Yoshikawa et al. ........ 73/23.2 |

* cited by examiner

*Primary Examiner* — John Fitzgerald
(74) *Attorney, Agent, or Firm* — Stites & Harbison PLLC; Jeffrey A. Haeberlin

(57) ABSTRACT

A sensor of the present invention includes a sensor element; a metallic shell; an outer tube member fixed to a rear end portion of the metallic shell; and a protective outer tube member covering an outer surface of the outer tube member. The outer tube member has a seal portion being circumferentially in contact with the protective outer tube member directly or via another member, and a front-side separation portion located frontward of the seal portion and spaced apart from and facing the protective outer tube member. A metal coating layer (plating layer) is formed on the outer surface of at least the front-side separation portion of the outer tube member.

14 Claims, 12 Drawing Sheets

[Fig. 1]
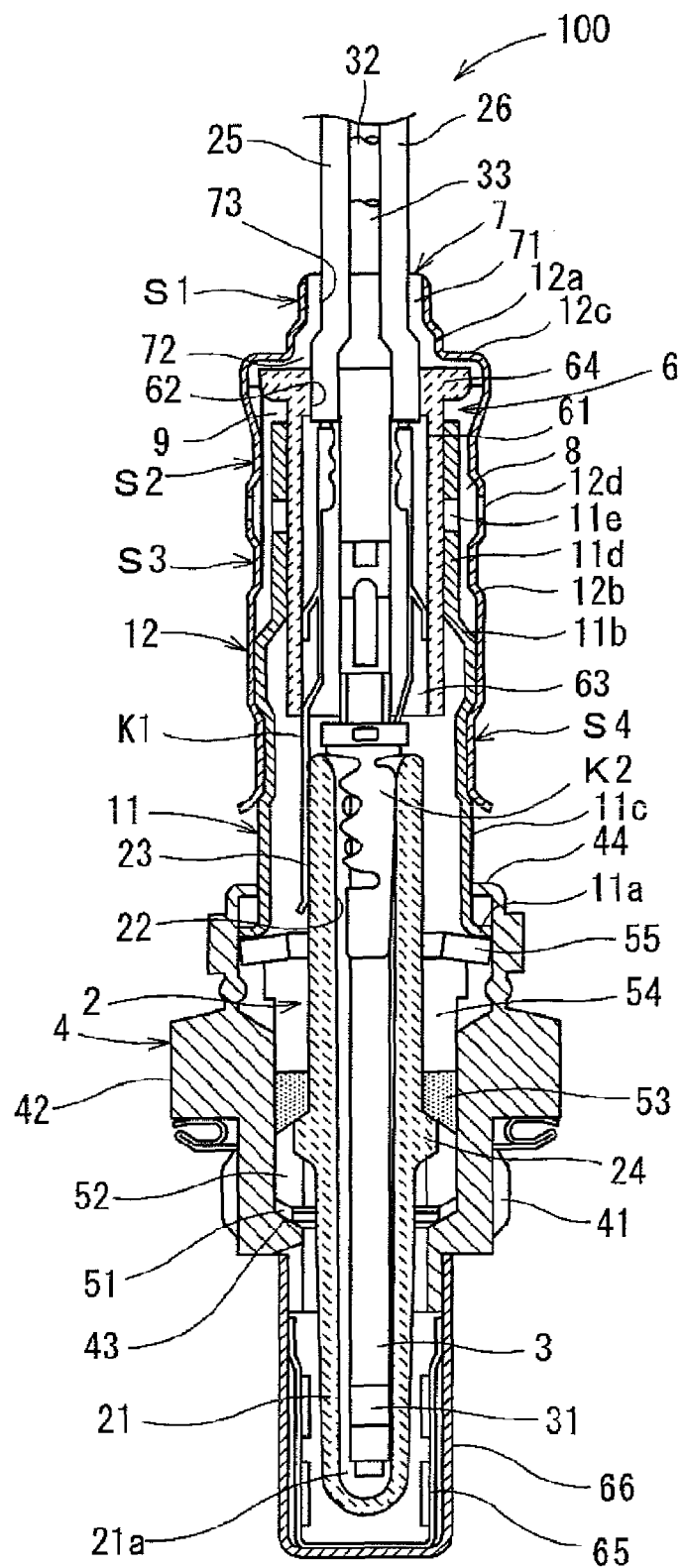

[Fig. 2]
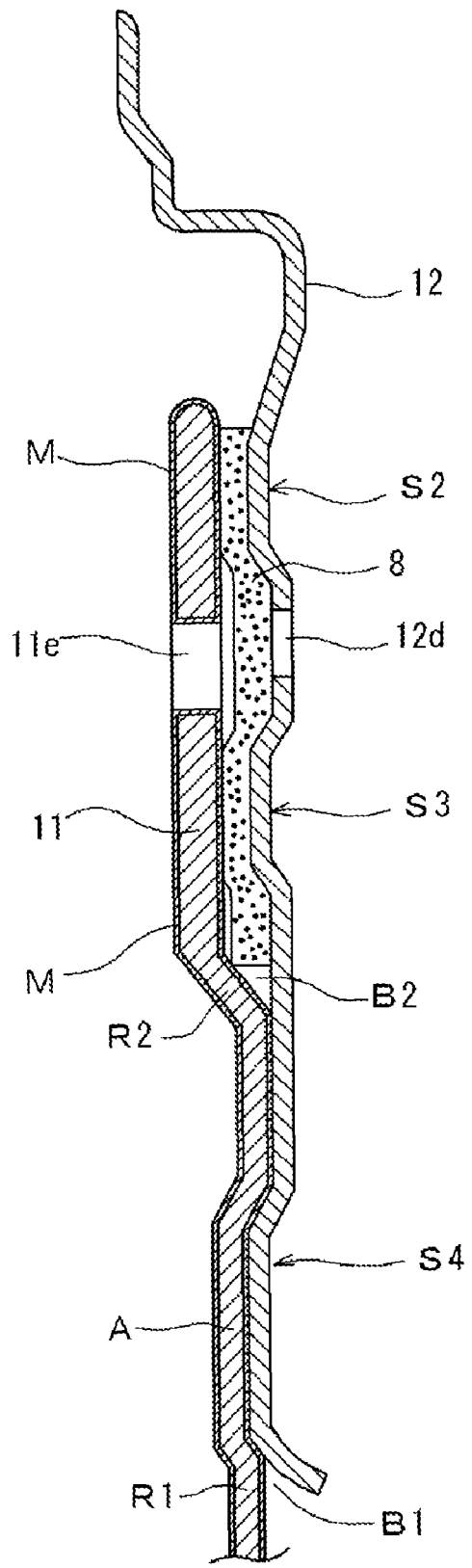

[Fig. 3]
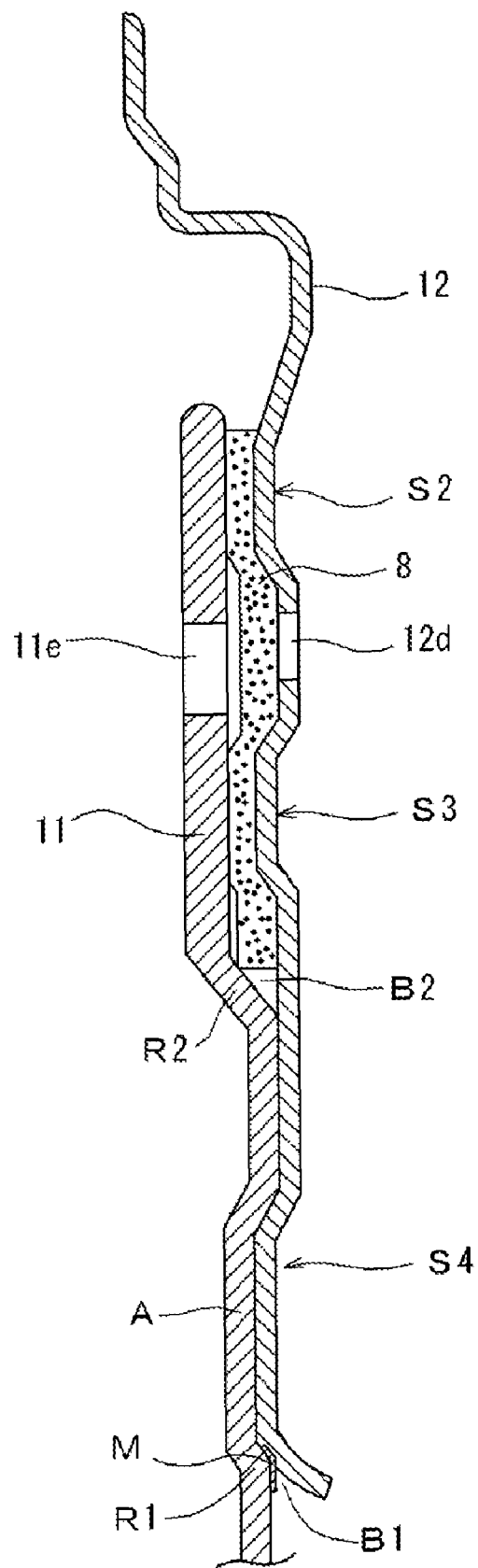

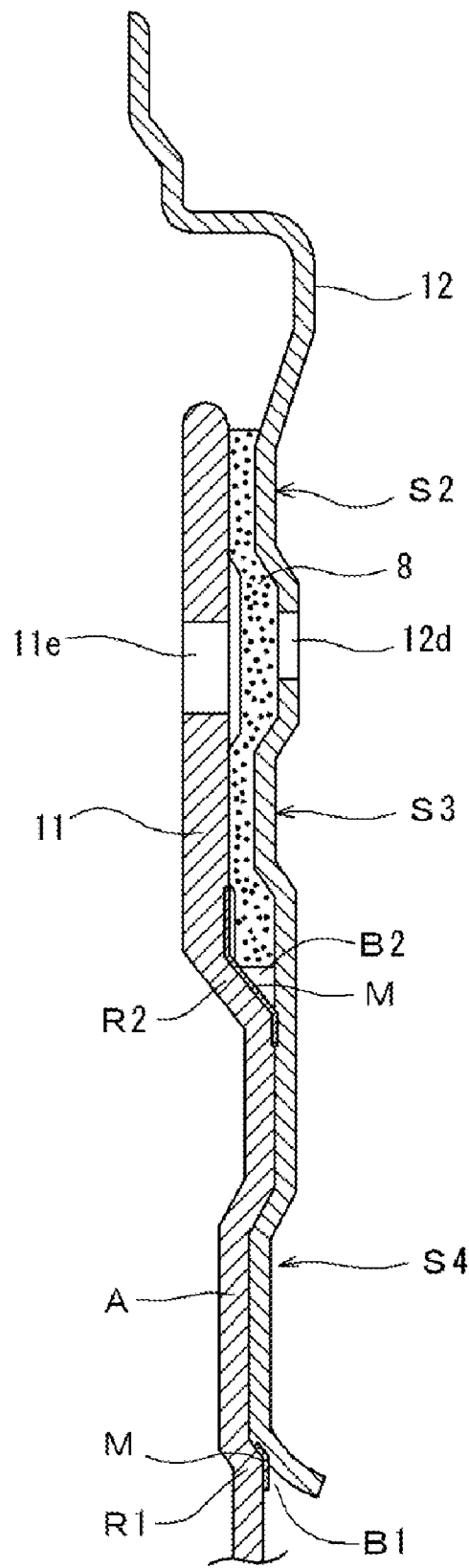
[Fig. 4]

[Fig. 5]
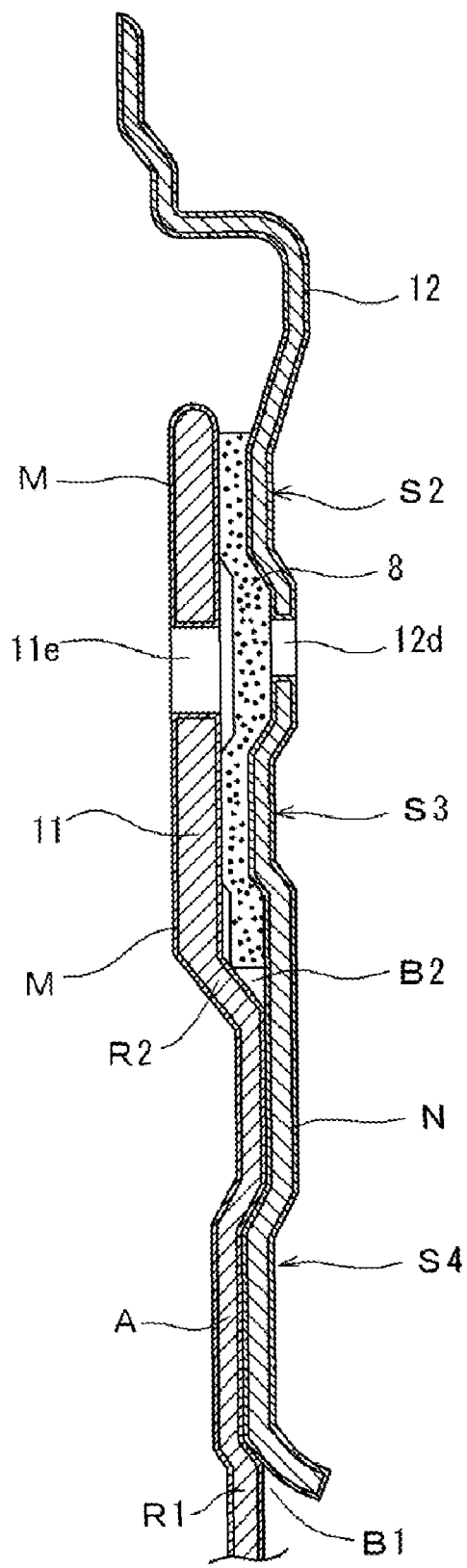

[Fig. 6]
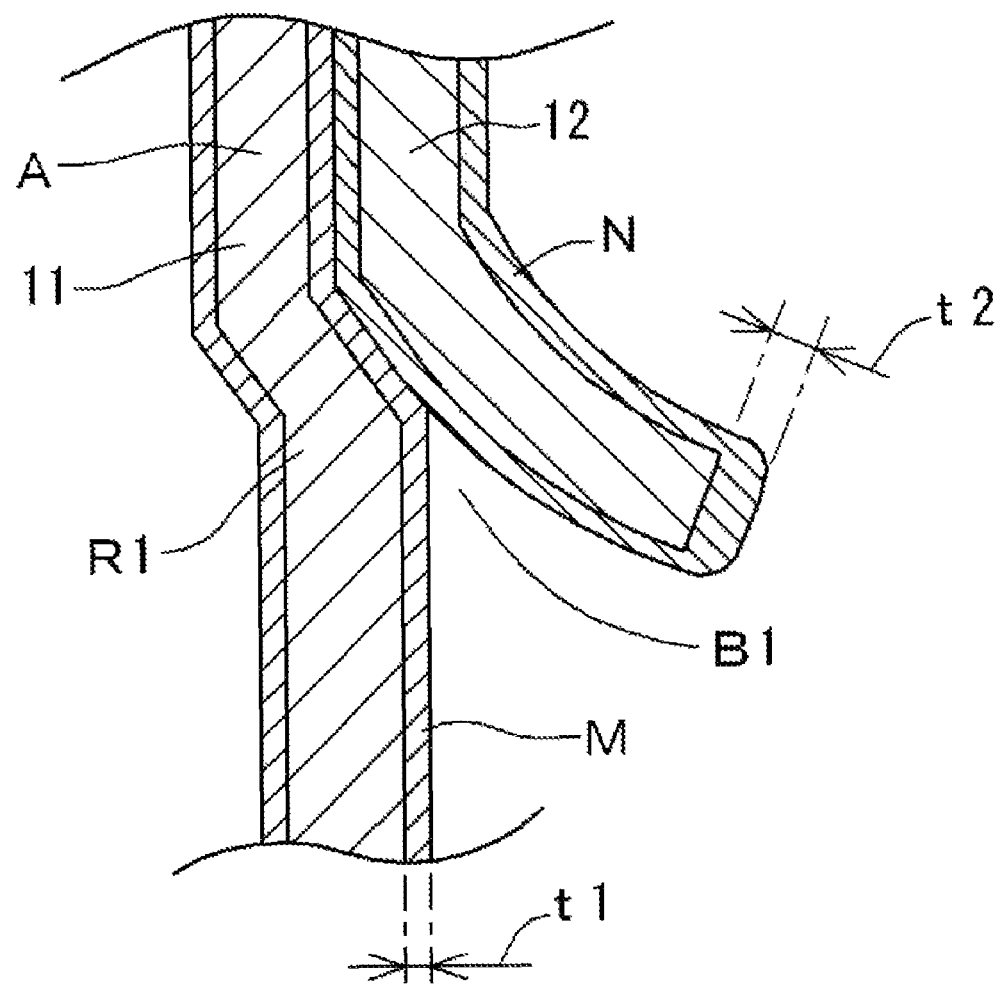

[Fig. 7]
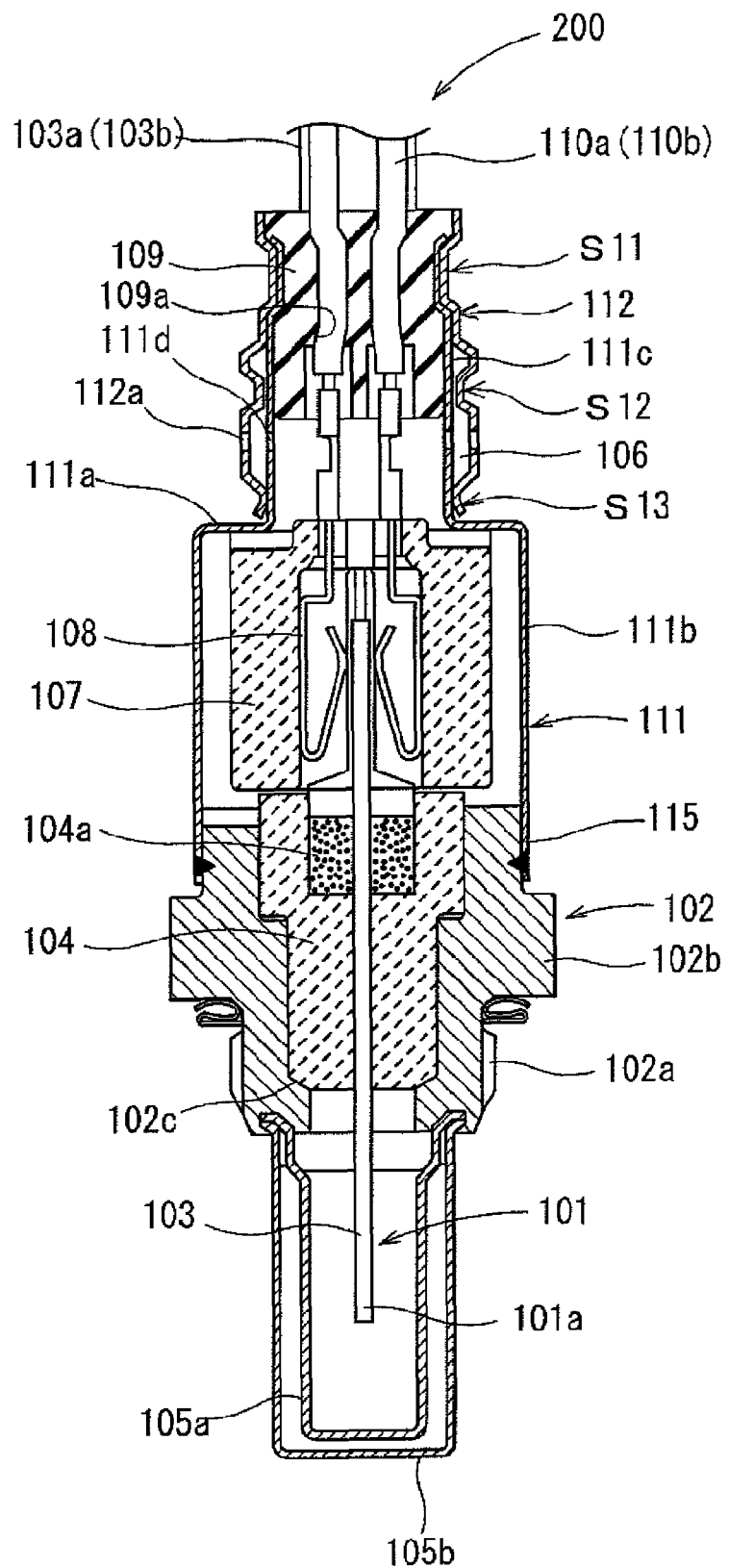

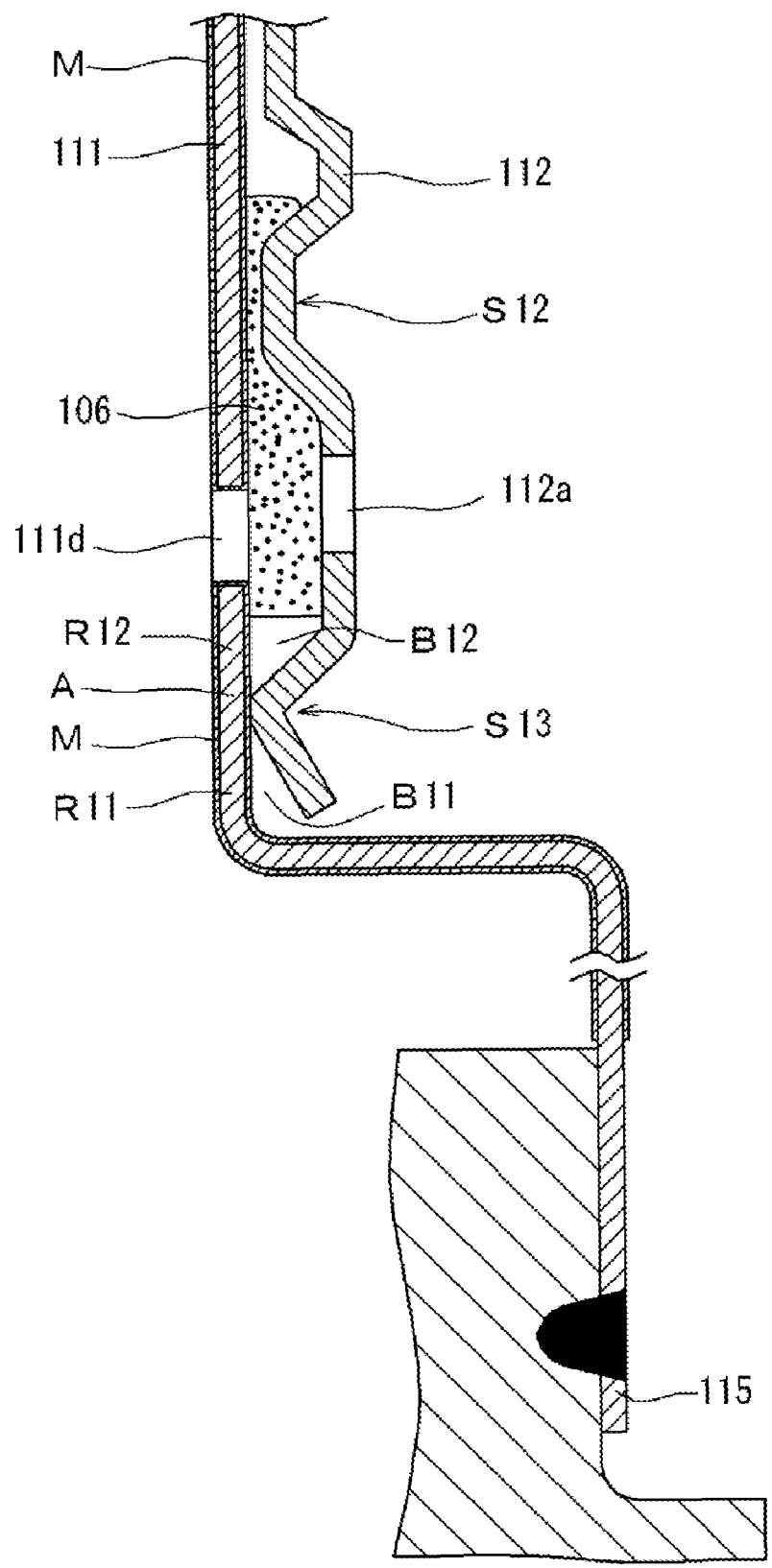
[Fig. 8]

[Fig. 9]
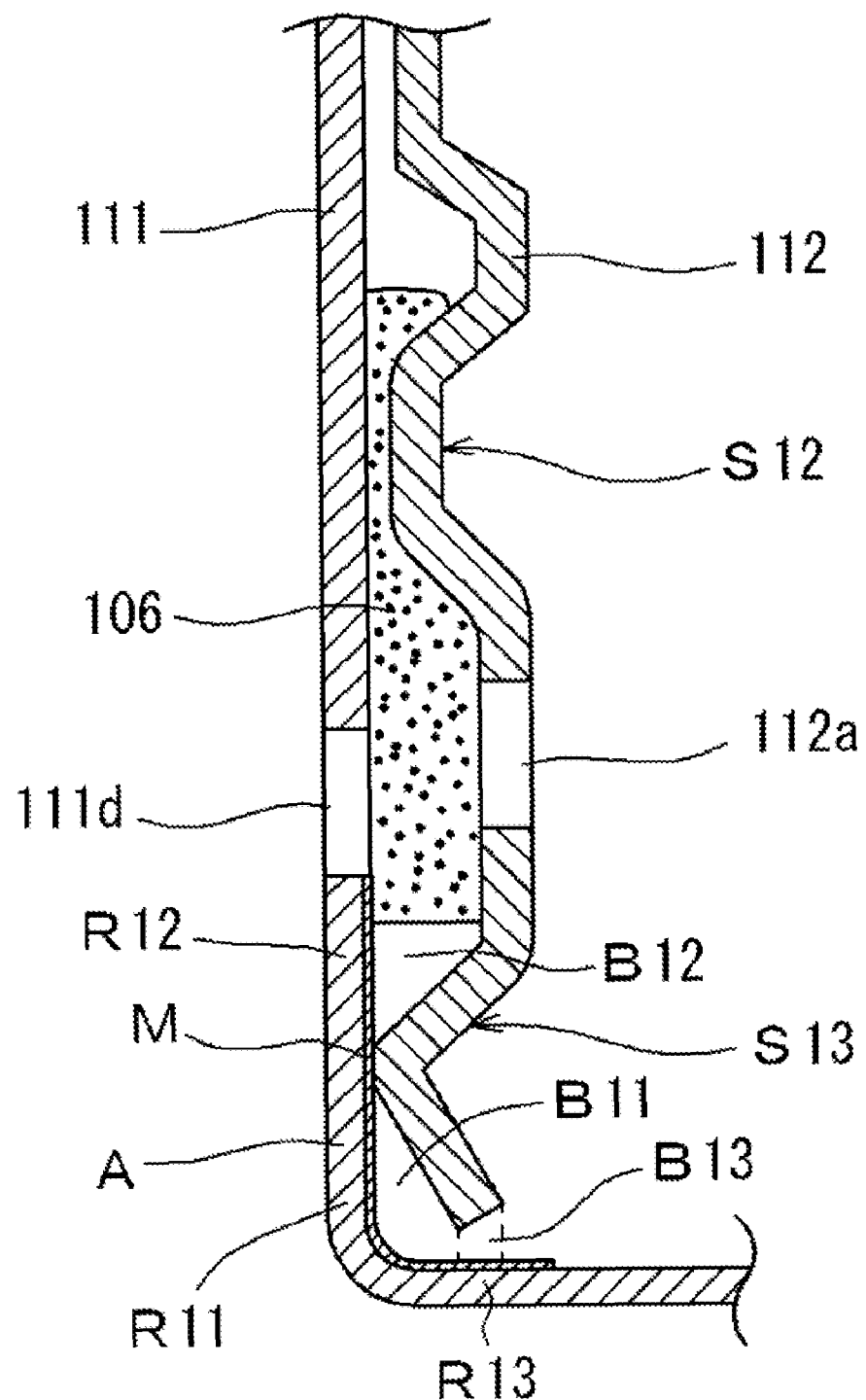

[Fig. 10]
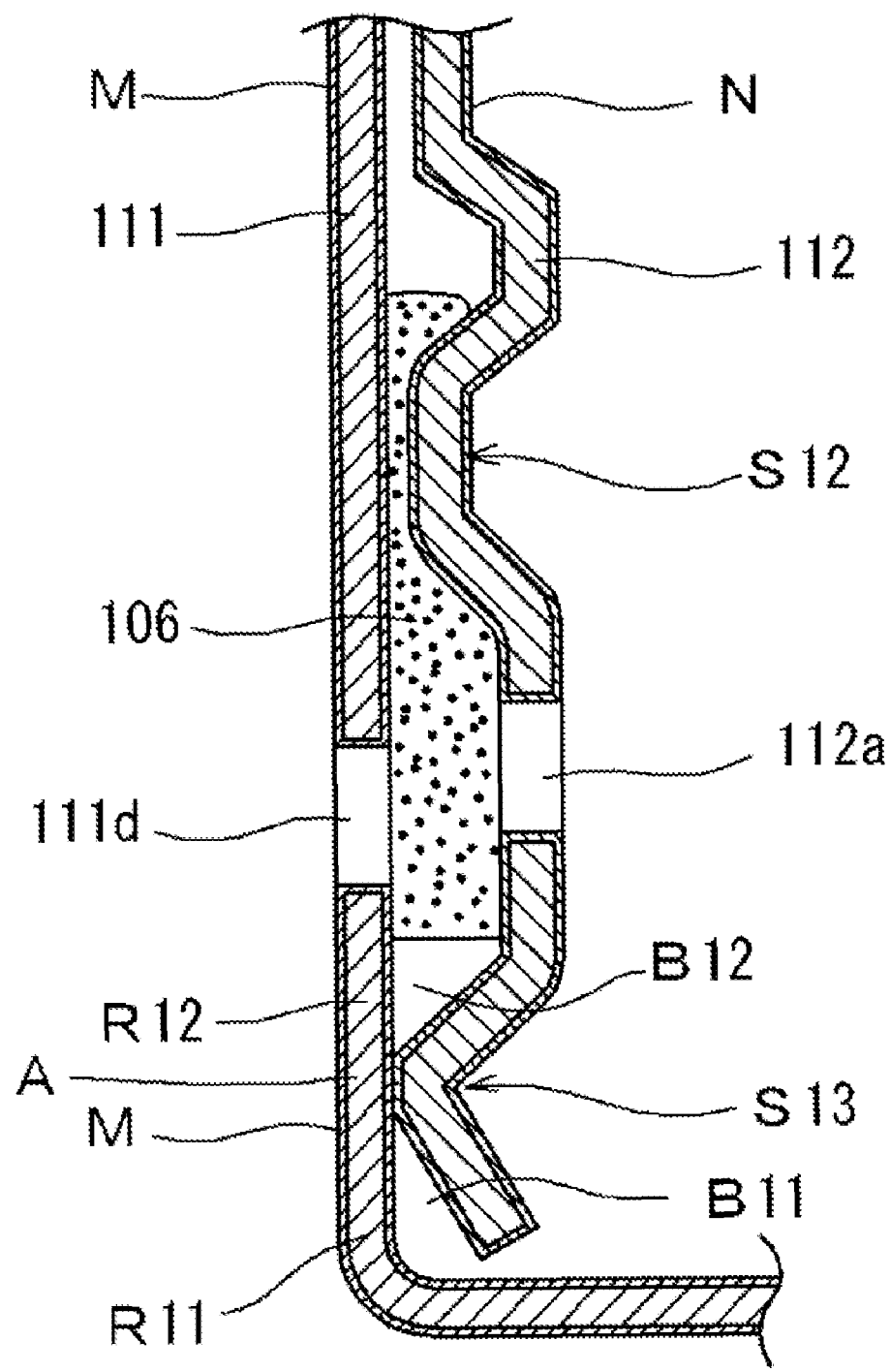

[Fig. 11]
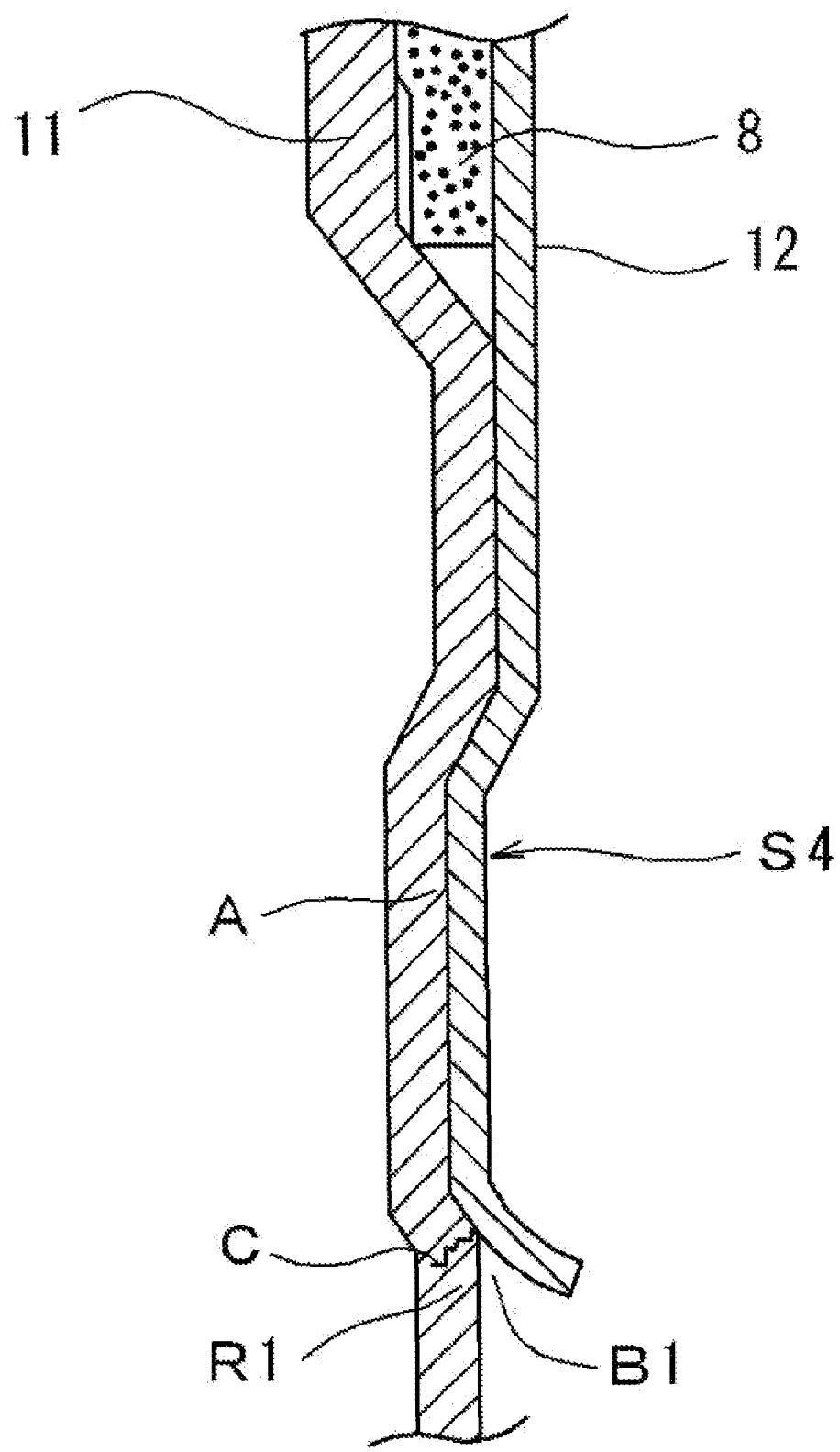

[Fig. 12]
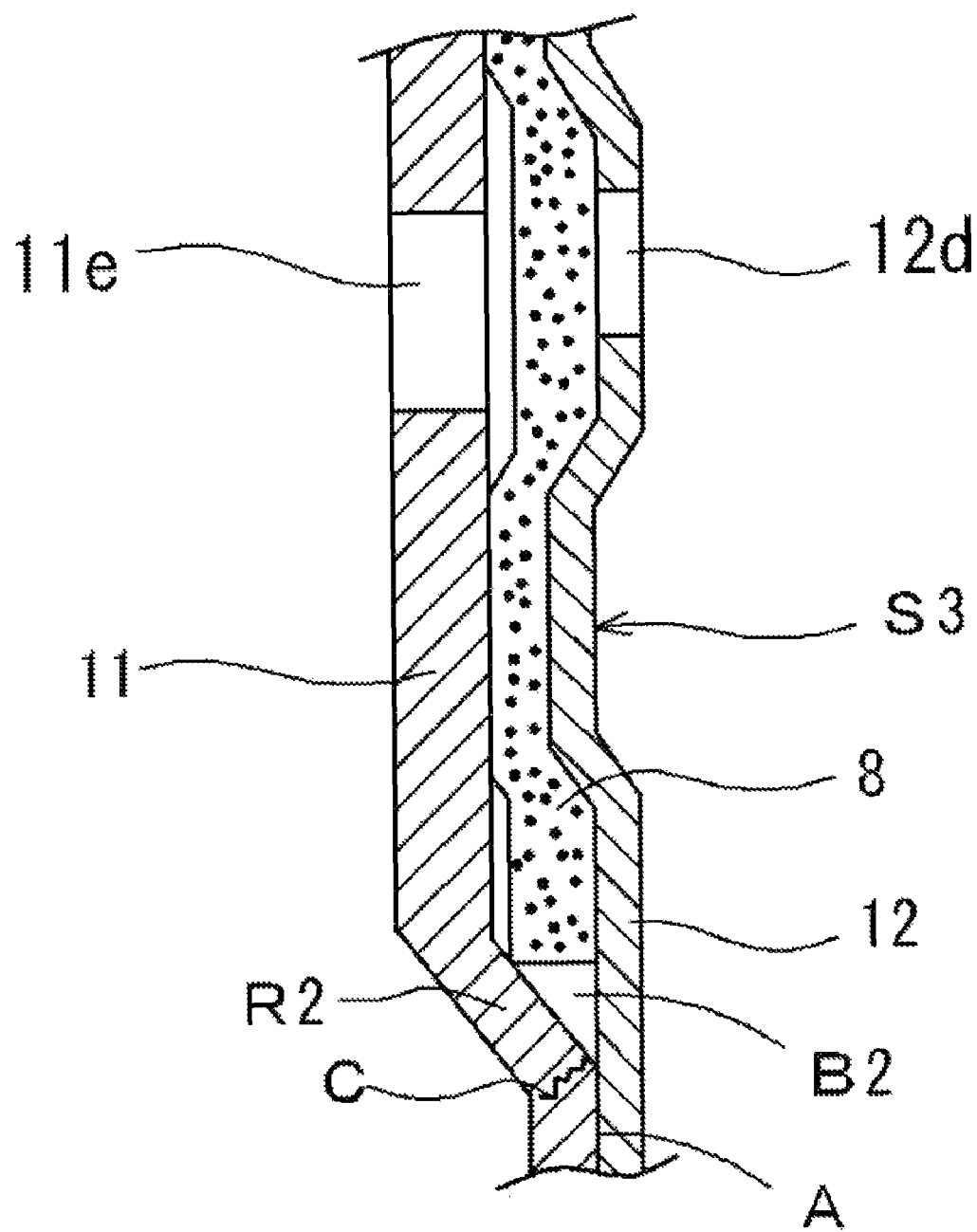

US 7,921,692 B2

SENSOR

TECHNICAL FIELD

The present invention relates to a sensor. More particularly, the invention relates to various sensors; for example, a gas sensor for detecting a component of an atmosphere to be measured, such as an oxygen sensor, a hydrocarbon sensor, or a nitrogen oxide sensor, and a temperature sensor for measuring the temperature of an atmosphere to be measured.

BACKGROUND ART

A conventionally known gas sensor has a structure in which a sensor element has a detecting portion provided at its front end for detecting a component of an atmosphere and is disposed in the interior of a metal casing. The metal casing is a combined entity of a plurality of tubular members, such as a metallic shell having an externally threaded portion used to mount the sensor; a protector, which is fixed to the metallic shell in such a manner as to cover the detecting portion of the sensor element projecting from the front end of the metallic shell; an outer tube member, which is fixed to a rear-end opening portion of the metallic shell and adapted to protect a portion of the sensor element which extends rearward from the opening portion; and a protective outer tube member, which is disposed in such a manner as to surround the outer tube member from radially outside via a water-repellent filter.

For use, such a gas sensor; for example, an oxygen sensor, is attached to an exhaust pipe or the like of an exhaust system of an automobile engine. According to a recent tendency, a catalytic device is attached to the exhaust pipe for decomposing organic substances contained in exhaust gas, and a gas sensor is attached downstream of the catalytic device for measuring a component of the exhaust gas from which organic substances have been removed. In this case, the gas sensor is disposed at a downstream position of the exhaust pipe, which extends rearward from the engine along a bottom section of the automobile. Accordingly, during travel of the automobile, a splash of water may adhere, in the form of a water droplet, to the outer surface of the gas sensor. Thus, in order to prevent entry of water or the like into the interior of the gas sensor, the plurality of tubular members must be reliably joined together so as to ensure sufficient watertightness of the gas sensor.

An example method for joining the above-mentioned plurality of tubular members together is a crimp-fixing process. For example, in a known gas sensor (refer to, for example, Patent Document 1), the protector is crimp-fixed to a front end portion of the metallic shell; a front end portion of the outer tube member is crimp-fixed to a rear end portion of the metallic shell; and a front end portion of the protective outer tube member which is fitted to the outer tube member is crimp-fixed to the outer tube member. In this gas sensor, for example, a connective crimped portion is provided at a front end portion of the protective outer tube member in such a manner as to be reduced in diameter radially inwardly. A front end portion of the connective crimped portion is in close contact with the outer surface of the outer tube member, thereby preventing penetration of water or the like along the interface between the outer tube member and the protective outer tube member.

[Patent Document 1] Japanese Patent Application Laid-Open (kokai) No. H11-352095

DISCLOSURE OF THE INVENTION

Problems to be Solved by the Invention

As shown in FIG. 11, in many cases, in order to allow a positional displacement within a tolerance, a front end portion of the protective outer tube member 12 which undergoes connective crimp-fixation in Patent Document 1 is located slightly apart in the rearward direction from the front end of the protective outer tube member 12. However, in many cases, crimping at the location causes outward warpage of a residual, front end portion of the protective outer tube member 12 located frontward of a connective crimped portion S4, thereby forming a small clearance B1 between the residual, front end portion of the protective outer tube member 12 and the outer surface of the outer tube member 11 (hereinafter referred to as the outer surface of a front-side separation portion R1). When the clearance B1 is formed, a water droplet or the like adhering to the outer circumferential surface of the gas sensor is attracted into the clearance B1 by capillarity. Water attracted into the clearance B1 stagnates therein over a long period of time by the effect of its surface tension.

Particularly, when an aqueous solution which contains a metal salt; for example, an aqueous solution in which salt is dissolved (hereinafter referred to as salt water), is attracted into the clearance B1, a chemical reaction occurs with the outer surface of the front-side separation portion R1 and with the inner surface of the protective outer tube member 12. This may cause corrosion of both the outer surface of the front-side separation portion R1 and the inner surface of the protective outer tube member 12. For example, in a cold region having a lot of snow, generally, a snow melting agent which contains calcium chloride is sprayed. In many cases, calcium chloride is dissolved in a puddle which is formed on the ground by melting snow. When an automobile runs over such a puddle, the following risk may be involved: a splash of salt water adheres to the surface of the gas sensor, and the salt water is attracted into the aforementioned clearance and stagnates therein, thereby causing corrosion of both the outer tube member 11 and the protective outer tube member 12. When the corrosion progresses, a crack C may arise in the front-side separation portion R1. As a result, salt water may penetrate into the interior of the outer tube member 11 through the crack C, potentially causing deterioration in detection accuracy of the sensor.

Further, as shown in FIG. 12, the protective outer tube member 12 has at least one atmosphere introduction hole 12d for introducing the atmosphere into the interior of the protective outer tube member 12; a filter 8 is disposed in a region corresponding to the atmosphere introduction hole 12d; and a seal portion A is formed frontward of the filter 8. In this case, because of the presence of the filter 8, usually, water does not enter the protective outer tube member 12 through the atmosphere introduction hole 12d. However, in some cases, water enters the protective outer tube member 12 through the atmosphere introduction hole 12d and stagnates in a clearance B2 between the protective outer tube member 12 and the outer tube member 11. Particularly, when salt water stagnates in the clearance B2, a chemical reaction occurs on the outer surface of the outer tube member 11 (hereinafter referred to as the outer surface of a rear-side separation portion R2). This may cause corrosion of the outer surface of the rear-side separation portion R2. When the corrosion progresses, the crack C may be generated in the outer tube member 11. As a result, salt water may penetrate into the interior of the outer tube member 11 through the crack C, potentially causing deterioration in detection accuracy of the sensor.

The present invention has been conceived for solving the above problems, and an object of the invention is to provide a sensor having a structure in which a plurality of tubular members are joined one another and characterized in that corrosion of an outer tube member by adhesion of water, such as salt water, is restrained, thereby preventing deterioration in detection accuracy of the sensor, which could otherwise result from penetration of salt water or the like into the interior of the outer tube member.

[Means for Solving the Problems]

The present invention is as follows:

1. A sensor comprising a sensor element which extends axially and whose front end portion is exposed to a gas to be measured, a metallic shell surrounding the sensor element, an outer tube member fixed to a rear end portion of the metallic shell, and a protective outer tube member covering an outer surface of the outer tube member, the outer tube member having a seal portion being circumferentially in contact with the protective outer tube member directly or via another member, and a front-side separation portion located frontward of the seal portion and spaced apart from and facing the protective outer tube member, wherein a metal coating layer is formed on an outer surface of at least the front-side separation portion of the outer tube member.

2. A sensor according to Par. 1, wherein at least a portion of an outer surface of the seal portion is exposed from the metal coating layer.

3. A sensor according to Par. 1 or 2, wherein the outer tube member has a joint portion joined to the metallic shell, and at least a portion of an outer surface of the joint portion is exposed from the metal coating layer.

4. A sensor according to any one of Pars. 1 to 3, wherein the metal coating layer is formed from a material which corrodes more easily than does the outer tube member.

5. A sensor according to any one of Pars. 1 to 4, wherein the outer tube member is formed from a stainless steel, and the metal coating layer is formed from a metal which contains aluminum, zinc, chromium, or nickel as a main component.

6. A sensor according to any one of Pars. 1 to 5, wherein the metal coating layer has a thickness of 1 µm to 50 µm inclusive.

7. A sensor according to any one of Pars. 1 to 4, wherein the outer tube member is formed from a stainless steel; the metal coating layer contains aluminum as a main component; and the metal coating layer has a thickness of 5 µm to 50 µm inclusive.

8. A sensor according to any one of Pars. 1 to 4, wherein the metal coating layer includes a first metal coating layer formed on the outer surface of the outer tube member, and a second metal coating layer formed on an outer surface of the first metal coating layer and differing in composition from the first metal coating layer.

9. A sensor according to Par. 8, wherein the outer tube member is formed from a stainless steel; the first metal coating layer contains nickel as a main component; and the second metal coating layer contains aluminum, zinc, or chromium as a main component.

10. A sensor according to Par. 8, wherein the outer tube member is formed from a stainless steel; the first metal coating layer contains aluminum or nickel as a main component; and the second metal coating layer contains gold as a main component.

11. A sensor according to any one of Pars. 1 to 10, wherein the outer tube member is formed from an austenitic stainless steel.

12. A sensor according to any one of Pars. 1 to 11, wherein the protective outer tube member has at least one atmosphere introduction hole for introducing the atmosphere into the interior of the protective outer tube member, and the outer tube member has at least one atmosphere introduction hole for introducing the atmosphere into the interior of the outer tube member; a filter is disposed between the atmosphere introduction hole of the protective outer tube member and the atmosphere introduction hole of the outer tube member, and the seal portion is formed frontward of the filter; and the outer tube member has a rear-side separation portion located rearward of the seal portion and frontward of the filter and spaced apart from and facing the protective outer tube member, and the metal coating layer formed on an outer surface of at least the rear-side separation portion of the outer tube member.

13. A sensor according to any one of Pars. 1 to 12, wherein the protective outer tube member has a front-end metal coating layer formed on a front end face of the protective outer tube member, and the front-end metal coating layer is greater in thickness than the metal coating layer.

14. A sensor according to any one of Pars. 1 to 13, wherein the outer tube member has a rear section surrounded by the protective outer tube member and having the seal portion and the front-side separation portion, a front section greater in diameter than the rear section, and a step section connecting the rear section and the front section; the step section has a facing portion which faces the protective outer tube member; and the metal coating layer is formed on an outer surface of the outer tube member which extends from the front-side separation portion to at least the facing portion.

[Effect of the Invention]

According to the sensor of the present invention, the metal coating layer is formed on the outer surface of at least the separation portion of the outer tube member. Thus, even when salt water or the like stagnates in the clearance which is formed between the inner surface of the protective outer tube member and the outer surface of the outer tube member (the outer surface of the front-side separation portion) and which extends frontward of the seal portion, corrosion of the outer tube member can be restrained, thereby preventing deterioration in detection accuracy of the sensor.

Particularly, in the case where the protective outer tube member is fixed to the outer tube member by crimping radially inward a portion of the protective outer tube member which is located rearward of the front end of the protective outer tube member, in many cases, a front end portion of the protective outer tube member which is located frontward of the crimped portion of the protective outer tube member warps outward, thereby forming a clearance between the inner surface of the front end portion of the protective outer tube member and the outer surface of the outer tube member. As a result, salt water is apt to stagnate in the clearance. However, the metal coating layer sufficiently restrains corrosion of the outer tube member, thereby preventing deterioration in detection accuracy of the sensor.

Preferably, the metal coating layer is not formed on at least a portion of the outer surface of the seal portion. By means of at least a portion of the seal portion of the outer tube member being in contact with the protective outer tube member without the metal coating layer intervening therebetween, the protective outer tube member is strongly joined to the outer tube member, thereby preventing a rotational movement of the protective outer tube member.

Further, preferably, the metal coating layer is not formed on at least a portion of the joint portion of the outer tube member, the joint portion being in contact with the metallic shell directly or via another member. By virtue of this, the outer tube member is strongly joined to the metallic shell, thereby preventing dropping-off of the outer tube member from the metallic shell.

Also, preferably, the metal coating layer is formed from a material which corrodes more easily than does the outer tube member. By virtue of this, even when salt water or the like stagnates in the clearance between the inner surface of the protective outer tube member and the outer surface of the separation portion of the outer tube member, the metal coating layer corrodes preferentially, thereby restraining corrosion of the outer tube member.

Further, preferably, the metal coating layer is formed from a metal which contains aluminum, zinc, chromium, or nickel as a main component. By virtue of this, the metal coating layer corrodes in preference to the outer tube member formed from a stainless steel. Thus, corrosion of the outer tube member is sufficiently restrained, thereby preventing deterioration in detection accuracy of the sensor.

Also, preferably, the metal coating layer has a thickness of 1 μm to 50 μm inclusive. The metal coating layer having a thickness of this range is sufficiently thick to restrain corrosion of the outer tube member. Thus, the outer tube member is reliably protected, thereby preventing deterioration in detection accuracy of the sensor.

Further, preferably, the outer tube member is formed from a stainless steel; the metal coating layer contains aluminum as a main component; and the metal coating layer has a thickness of 5 μm to 50 μm inclusive. In this case, since the metal coating layer is thick, corrosion of the outer tube member is sufficiently restrained. Also, since the outer tube member is formed from a stainless steel, iron elements diffuse from the outer tube member into the metal coating layer which contains aluminum as a main component, thereby forming a diffusion phase. This enhances adherence between the metal coating layer and the outer tube member. Therefore, in spite of the metal coating layer being thick, exfoliation of the metal coating layer is restrained.

Also, preferably, the metal coating layer includes the first metal coating layer formed on the outer surface of the outer tube member, and the second metal coating layer formed on the outer surface of the first metal coating layer and differing in composition from the first metal coating layer. In this case, by means of selective combination of compositions of the first and second metal coating layers, adherence between the metal coating layer and the outer tube member can be enhanced, and corrosion of the outer tube member can be sufficiently restrained, thereby preventing deterioration in detection accuracy of the sensor.

Further, preferably, the outer tube member is formed from a stainless steel; the first metal coating layer contains nickel as a main component; and the second metal coating layer contains aluminum, zinc, or chromium as a main component. When the first metal coating layer contains nickel as a main component, the first metal coating layer can sufficiently adhere to the outer tube member formed from a stainless steel. That is, the second metal coating layer can adhere to the outer metal member via the first metal coating layer. Also, when the second metal coating layer contains aluminum, zinc, or chromium as a main component, the second metal coating layer corrodes more easily than does the first metal coating layer. Thus, after the second metal coating layer corrodes, the first metal coating layer corrodes. Therefore, corrosion of the outer tube member can be sufficiently restrained, thereby preventing deterioration in detection accuracy of the sensor.

Further, preferably, the outer tube member is formed from a stainless steel; the first metal coating layer contains aluminum or nickel as a main component; and the second metal coating layer contains gold as a main component. In this case, the second metal coating layer having high corrosion resistance sufficiently protects the outer tube member. Even when pitting corrosion or the like occurs on the second metal coating layer, the first metal coating layer protects the outer tube member. Thus, the outer tube member is not immediately corroded, thereby preventing deterioration in detection accuracy of the sensor.

The main component of the metal coating layer means an element that is contained in the greatest amount in the metal coating layer. That is, in an analyzed composition of the metal coating layer, an element whose content is the highest among component elements of the metal coating layer is considered to be the main component of the metal coating layer.

Also, in the case where the outer tube member is formed from an austenitic stainless steel, even though an austenitic stainless steel is ranked low in corrosion resistance among stainless steels, the metal coating layer sufficiently protects the outer tube member, thereby preventing deterioration in detection accuracy of the sensor.

Further, even in the case where the protective outer tube member has at least one atmosphere introduction hole for introducing the atmosphere into the interior of the protective outer tube member; the outer tube member has at least one atmosphere introduction hole for introducing the atmosphere into the interior of the outer tube member; the filter is disposed between the atmosphere introduction hole of the protective outer tube member and the atmosphere introduction hole of the outer tube member; and the seal portion is formed frontward of the filter, the metal coating layer is also formed on the outer surface of the rear-side separation portion of the outer tube member, the rear-side separation portion extending rearward of the seal portion and being spaced apart from and facing the protective outer tube member. Thus, even on the rear side of the seal portion, even when salt water or the like stagnates in the clearance between the protective outer tube member and the outer tube member, corrosion of the outer tube member can be restrained, thereby preventing deterioration in detection accuracy of the sensor.

Also, preferably, the protective outer tube member has the front-end metal coating layer formed on the front end face of the protective outer tube member, and the front-end metal coating layer is greater in thickness than the metal coating layer. The front end face of the protective outer tube member is a fracture plane and is thus most likely to corrode in the protective outer tube member. Thus, the font-end metal coating layer is formed on the front end face and is rendered thicker than the metal coating layer, whereby corrosion of the protective outer metal member can also be prevented.

Further, preferably, the outer tube member has the rear section surrounded by the protective outer tube member, the front section greater in diameter than the rear section, and the step section connecting the rear section and the front section; the step section has the facing portion which faces the protective outer tube member; and the metal coating layer is formed on the outer surface of the outer tube member which extends from the front-side separation portion to at least the facing portion. A certain outer tube member has the step section for connecting the rear section and the front section, which is greater in diameter than the rear section. In this case, the protective outer tube member is disposed radially outward of the rear section of the outer tube member. In such an arrangement, a clearance is also formed between the step section of the outer tube member and the front end of the protective outer tube member. Accordingly, salt water or the like may stagnate in the clearance. However, by means of the metal coating layer extending up to the outer surface of the facing portion of the step section, there can be restrained corrosion of the outer tube member, which could otherwise result from salt water which stagnates in the clearance between the step section and the protective outer tube member.

BEST MODE FOR CARRYING OUT THE INVENTION

A gas sensor 100, which is an embodiment of a sensor of the present invention, will next be described with reference to the drawings.

[1] Gas sensor of a First Embodiment

FIG. 1 is a schematic, sectional view of the gas sensor 100 according to the present embodiment. For use, the gas sensor 100 is attached to an exhaust pipe of an automobile. An example of the gas sensor 100 is an oxygen sensor for detecting the concentration of oxygen contained in exhaust gas flowing through the exhaust pipe. The oxygen sensor will be described below in detail.

The gas sensor 100 includes a sensor element 2, which extends axially and has a closed-bottomed tubular shape whose front end is closed; a metallic shell 4, which surrounds the sensor element 2 and holds the sensor element 2 on the inner side thereof; an outer tube member 11, which is fixed to a rear end portion of the metallic shell 4; and a protective outer tube member 12, which covers an outer surface of the outer tube member 11.

In the present embodiment, with respect to the axial direction of the sensor 100 of FIG. 1, a side toward a front end portion of the sensor element 2 which is exposed to a gas to be measured (exhaust gas) (a side toward a bottom portion of a solid electrolyte body 21 having a closed-bottomed tubular shape; a lower side in FIG. 1) is referred to as the "front side," and a side opposite the front side (an upper side in FIG. 1) is referred to as the "rear side."

(1) Sensor element

The sensor element 2 includes the solid electrolyte body 21, which has a closed-bottomed tubular shape whose front end is closed and which is formed from an oxygen-ion-conductive ceramic which contains, as a main component, partially stabilized zirconia or the like with yttria or the like in solution as a stabilizer; a porous inner electrode layer 22, which is formed from Pt or a Pt alloy on substantially the entire inner surface of the solid electrolyte body 21; and a porous outer electrode layer 23, which is formed on the outer surface of the solid electrolyte body 21 in a manner similar to that for forming the inner electrode layer 22.

The outer electrode layer 23 is coated with a porous electrode protection layer formed from a heat-resistant ceramic, such as alumina-magnesia-spinel. Further, the sensor element 2 has an engagement flange portion 24 projecting radially outward and located at a substantially intermediate position with respect to the axial direction. A rodlike ceramic heater 3 having a heat-generating portion 31, into which a heat-generating resistor is incorporated, is inserted into the solid electrolyte body 21 in such a manner that the heat-generating portion 31 is located in a bottom portion of the solid electrolyte body 21. Electricity is applied to the ceramic heater 3 through heater lead wires 32, 33, which will be described later, whereby the heat-generating portion 31 generates heat, thereby activating the sensor element 2 through application of heat.

(2) Metallic shell

The metallic shell 4 includes a threaded portion 41 adapted to attach the gas sensor 100 to an attachment portion of an exhaust pipe, and a hexagonal portion 42 to which an attachment tool is applied in attachment to the attachment portion of the exhaust pipe. The metallic shell 4 has a shell-side step portion 43 which is formed on the inner circumferential surface of a front end portion of the metallic shell 4 in such a manner as to project radially inward. A support member 52 made of alumina is engaged with the shell-side step portion 43 via a packing 51. The sensor element 2 is supported by the metallic shell 4 in such a manner that its engagement flange portion 24 is supported by the support member 52. Further, an inorganic filler, such as talc powder, is filled into a space between the outer surface of the sensor element 2 and an inner surface of the metallic shell 4 located rearward of the support member 52, thereby forming a filler portion 53. A sleeve 54 made of alumina, and an annular ring 55 are sequentially disposed rearward of the filler portion 53 in a coaxially inserted manner.

Metallic double-structured protectors 65, 66 are externally welded to a front end portion of the metallic shell 4 in such a manner as to surround a front end portion of the sensor element 2 which projects from the front end of the metallic shell 4. Each of the protectors 65, 66 has a plurality of gas intake holes. Exhaust gas flows in through the gas intake holes and undergoes detection of the concentration of oxygen contained therein.

(3) Outer tube member

Material for the outer tube member 11 is not particularly limited. However, a material having sufficient strength and corrosion resistance is preferred. Usually, stainless steel is used. The type of stainless steel is also not particularly limited. Various types of stainless steel can be used. For example, an austenitic stainless steel, such as SUS304L, which exhibits excellent weldability, among others, can be used. A front end portion of the outer tube member 11 is fixedly inserted into a rear end portion of the metallic shell 4. The outer tube member 11 is fixed to the metallic shell 4 as follows: while a diametrally expanded front open end portion 11a of the outer tube member 11 is in contact with the annular ring 55, a shell-side outer end portion 44 of the metallic shell 4 is crimped inwardly.

In the gas sensor 100, as a result of crimping of the shell-side rear end portion 44 of the metallic shell 4, the inorganic filler, such as talc powder, is compressively filled via the sleeve 54, thereby forming the filler portion 53. Thus, the sensor element 2 is held watertight in the tubular, metallic shell 4.

Further, the outer tube member 11 has an outer-tube step section 11b which is formed at a substantially middle position with respect to its axial direction; a portion of the outer tube member 11 located frontward of the outer-tube step section 11b serves as an outer-tube front-barrel section 11c; and a portion of the outer tube member 11 located rearward of the outer-tube step section 11b serves as an outer-tube rear-barrel section 11d. The outer-tube rear-barrel section 11d is slightly smaller in inner and outer diameters than the outer-tube front-barrel section 11c. The inner diameter of the outer-tube rear-barrel section 11d is slightly greater than the outer diameter of a separator body section 61 of a separator 6, which will be described later. The outer-tube rear-barrel section 11d has a plurality of atmosphere introduction holes 11e formed therein at predetermined circumferential intervals.

(4) Protective outer tube member

Material for the protective outer tube member 12 is not particularly limited. However, a material having sufficient strength and corrosion resistance is preferred. Usually, stainless steel is used. The type of stainless steel is also not particularly limited. Various types of stainless steel can be used. For example, an austenitic stainless steel, such as SUS304L, which exhibits excellent deep-drawability, among others, can be used. A plate material of stainless steel, such as SUS304L, is deep-drawn into a tubular shape so as to form the protective outer tube member 12 having the following sections: a protective-outer-tube rear section 12a having a rear-end opening portion for allowing communication therethrough between the interior and the exterior of the section; a protective-outer-tube front section 12b which is coaxially fitted and connected to the outer tube member 11 from the rear side; and a protective-outer-tube diametral-transition section 12c extending between the protective-outer-tube rear section 12a and the protective-outer-tube front section 12b.

The protective-outer-tube front section 12b of the protective outer tube member 12 has a plurality of atmosphere introduction holes 12d formed therein at predetermined circumferential intervals. A filter 8, which is described below, is disposed between the outer-tube rear-barrel section lid of the outer tube member 11 and the protective-outer-tube front section 12b.

The protective-outer-tube rear section 12a has a crimped portion S1 for fixing an elastic seal member 7, which will be described later, in a watertight manner.

(5) Filter

While the protective outer tube member 12 has the atmosphere introduction holes 12d formed therein, and the outer tube member 11 has the atmosphere introduction holes 11e formed therein, the filter 8 is disposed between the protective outer tube member 12 and the outer tube member 11 at at least a position corresponding to the atmosphere introduction holes 12d, 11e. The filter 8 can prevent entry of water through the atmosphere introduction holes 11e. The filter 8 is formed from a porous material of synthetic resin fiber or the like, preferably a porous material of fiber exhibiting excellent water repellency. An example material for the filter 8 is a porous material of polytetrafluoroethylene (GORE-TEX, a product of Japan Gore-Tex Inc.). While restraining permeation of water or a liquid which contains a large amount of water, the filter 8 permits gas, such as the air, to readily permeate therethrough.

(6) Structure of connection between the outer tube member and the protective outer tube member As shown in FIG. 1, the protective outer tube member 12 and the outer tube member 11 are fixed together by means of a second crimped portion S2 and a third crimped portion S3. The second crimped portion S2 is formed by crimping radially inward, via the filter 8, at least a portion of the protective-outer-tube front section 12b of the protective outer tube member 12 which is located rearward of the atmosphere introduction holes 12d. The third crimped portion S3 is formed by crimping radially inward, via the filter 8, at least a portion of the protective-outer-tube front section 12b of the protective outer tube member 12 which is located frontward of the atmosphere introduction holes 12d. In this case, the disposed filter 8 is compressed and held between the outer tube member 11 and the protective outer tube member 12. The protective-outer-tube front section 12b of the protective outer tube member 12 is disposed in such a manner as to be externally fitted to the outer-tube front-barrel section 11c. Further, a front end portion of the protective-outer-tube front section 12b and the outer-tube front-barrel section 11c are crimped together; i.e., the front end portion of the protective-outer-tube front section 12b is crimped radially inward, thereby forming the connective crimped portion S4, which is a radially inwardly diameter-reduced portion.

As mentioned above, the protective outer tube member 12 is fixedly crimped to the outer tube member 11, whereby the outer tube member 11 and the protective outer tube member 12 are strongly fixed and connected together. The atmosphere which serves as a reference gas is introduced into the interior of the outer tube member 11 through the atmosphere introduction holes 12d, the filter 8, and the atmosphere introduction holes 11e and is then introduced into a bottom portion 21a of the solid electrolyte body 21. Meanwhile, the filter 8 restrains entry of water, thereby hindering entry of water into the interior of the outer tube member 11.

The outer tube member 11 and the protective outer tube member 12 can be connected and fixed together not only by crimping, but also by welding, such as resistance welding, laser beam welding, and electron beam welding, and press fit.

(7) Structure inside the outer tube member and the protective outer tube member

As shown in FIG. 1, the substantially cylindrical separator 6 is disposed inside the outer-tube rear-barrel section 11d of the outer tube member 11. The separator 6 has lead-wire insertion holes 62 which extend therethrough in the front-rear direction and through which element lead wires 25, 26 and the heater lead wires 32, 33 extend respectively. The separator 6 has a closed-bottomed retaining hole 63 which opens at the front end face of the separator 6 and extends axially. A rear end portion of the ceramic heater 3 is inserted into the retaining hole 63. By means of the rear end face of the ceramic heater 3 coming into contact with the bottom surface of the retaining hole 63, the ceramic heater 3 is axially positioned.

Further, the separator 6 includes a separator body portion 61, which is fitted into a rear end portion of the outer tube member 11, and a separator flange portion 64, which extends radially outward from a rear end portion of the separator body portion 61. That is, the separator 6 is disposed inside the protective outer tube member 12 in such a state that the separator body portion 61 is fitted into the outer tube member 11 and that the separator flange portion 64 is supported on the rear end face of the outer tube member 11 via an annular seal member 9 made of fluorine-containing rubber or the like.

Meanwhile, the elastic seal member 7 made of fluorine-containing rubber or the like having excellent heat resistance is disposed on the rear side of the separator 6. The elastic seal member 7 includes a body portion 71 and a seal-member flange portion 72, which extends radially outward from a front end portion of the body portion 71. The body portion 71 has four lead-wire insertion holes 73 extending axially therethrough. The elastic seal member 7 is inserted into a rear end portion of the protective outer tube member 12 as mentioned above. The rear end portion of the protective outer tube member 12 is crimped, thereby forming the crimped portion S1. By this procedure, the elastic seal member 7 is fixed in the protective outer tube member 12.

Further, the element lead wires 25, 26 and the heater lead wires 32, 33 extend through the respective lead-wire insertion holes 62 of the separator 6 and through the respective lead-wire insertion holes 73 of the elastic seal member 7 and outwardly from inside the outer tube member 11 and the protective outer tube member 12.

The four lead wires 32, 33, 25, 26 are connected to unillustrated respective external connectors, through which electrical signals flow between external equipment, such as an ECU, and the lead wires 32, 33, 25, 26.

Although unillustrated in detail, each of the lead wires 32, 33, 25, 26 has a structure in which a conductor is coated with an insulation film made of resin. Rear end portions of the conductors are connected to respective connector terminals of the connectors. A front end portion of the conductor of the element lead wire 25 is crimp-connected to a rear end portion of a metal terminal K1, which is externally attached to the outer surface of the solid electrolyte body 21. A front end portion of the conductor of the element lead wire 26 is crimp-connected to a rear end portion of a metal terminal K2, which is press-fitted into the solid electrolyte body 21. By virtue of the connections, the element lead wire 25 is electrically connected to the outer electrode layer 23 of the sensor element 2, and the element lead wire 26 is electrically connected to the inner electrode layer 22 of the sensor element 2. Meanwhile, front end portions of the conductors of the heater lead wires 32, 33 are connected to paired heater metal-terminals, respectively, joined to a heat-generating resistor of the ceramic heater 3.

(8) Plating layer

As mentioned previously in (6), the outer tube member 11 and the protective outer tube member 12 are connected and fixed together by means of crimping at the connective crimped portion S4 (see FIG. 2). The outer tube member 11 has a seal portion A (a portion corresponding to the connective crimped portion S4) whose outer circumferential surface is in contact with the protective outer tube member 12 for providing a seal between the outer tube member 11 and the protective outer tube member 12, and a front-side separation portion R1 which extends frontward of the seal portion A and is spaced apart from and faces the protective outer tube member 12.

The outer tube member 11 also has a rear-side separation portion R2 which extends rearward of the seal portion A and is spaced apart from and faces the protective outer tube member 12.

As shown in FIG. 2, a plating layer M (corresponding to the metal coating layer of the present invention) is formed on the outer surface of the outer tube member 11 including the outer surface of the front-side separation portion R1 and the outer surface of the rear-side separation portion R2. By virtue of the plating layer M formed on the outer surface of the front-side separation portion R1, even when salt water or the like stagnates in a clearance B1 between the inner surface of the protective outer tube member 12 and the outer surface of the front-side separation portion R1, corrosion of the outer tube member 11 can be restrained, thereby preventing deterioration in detection accuracy of the sensor.

Also, by virtue of the plating layer M formed on the outer surface of the rear-side separation portion R2, even when salt water or the like stagnates in a clearance B2 between the inner surface of the protective outer tube member 12 and the outer surface of the rear-side separation portion R2, corrosion of the outer tube member 11 can be restrained, thereby preventing deterioration in detection accuracy of the sensor.

When the plating layer M is formed from a material which corrodes more easily than does the outer surface of the outer tube member 11, the plating layer M corrodes preferentially, thereby restraining corrosion of the outer tube member 11. By using gold or a like material which does not easily corrode, to form the plating layer M, corrosion of the outer tube member 11 can also be restrained. In the case of selection of material for the plating layer M on a criterion whether or not the material corrodes easily, material for the outer tube member 11 and material for the plating layer M can be selected on the basis of their individual ionization tendencies.

No particular limitation is imposed on material for the plating layer M. The plating layer M may be formed from a material which has a high ionization tendency and corrodes easily, or a material which has a low ionization tendency and does not corrode easily. Also, the plating layer M may contain a single metal or two or more metals, particularly two metals. Preferably, the plating layer M is formed from a material which has such a high ionization tendency as to corrode in preference to the outer tube member 11, thereby restraining corrosion of the outer tube member 11. In the case where the outer tube member 11 is formed from stainless steel, preferably, the plating layer M is formed from a metal which contains aluminum, zinc, chromium, or nickel as a main component. Specific examples of such a plating layer M include an aluminum plating layer, a zinc plating layer, a chromium plating layer, a nickel plating layer, a zinc-nickel plating layer, and a nickel-chromium plating layer. In the case where the outer tube member 11 is formed from stainless steel, these kinds of plating layers M corrode in preference to the outer tube member 11, thereby restraining corrosion of the outer tube member 11. Ionization tendencies of the metals contained in the above-mentioned plating layers are in the following relation: aluminum>zinc>chromium>nickel. Preferably, these plating layers M are selected as appropriate on the basis of a required corrosion-restraining action.

Further, more preferably, the plating layer M is formed from a material which adheres to and does not easily exfoliate from the outer tube member 11; can be readily formed into a film having a predetermined thickness; and can protect the outer tube member 11 from corrosion over a long period of time. In the case where the outer tube member 11 is formed from stainless steel, the plating layer M is formed from, for example, a metal which contains aluminum or nickel as a main component. Specific examples of such a plating layer M include an aluminum plating layer and a nickel plating layer.

A method for forming the plating layer M is not particularly limited. The method may be an electroplating process, an electroless plating process, a hot dipping process, or the like. An ordinary plating process associated with a material used to form the plating layer M can be employed.

No particular limitation is imposed on the thickness of the plating layer M, so long as corrosion of the outer tube member 11 is sufficiently restrained. Depending on a metal contained therein, the plating layer M has a thickness of preferably 1 μm to 50 μm inclusive, more preferably 3 μm to 20 μm inclusive. When the thickness of the plating layer M is less than 1 μm, depending on a material used to form the plating layer M, the plating layer M may fail to yield a sufficient action or effect of restraining corrosion. When the thickness of the plating layer M is in excess of 50 μm, at the time of connecting and fixing the outer tube member 11 and the protective outer tube member 12 together by, for example, crimping, the plating layer M may crack, resulting in exfoliation of the plating layer M from the surface of the outer tube member 11.

In the case where the outer tube member 11 is formed from stainless steel, and the plating layer M is formed from a metal which contains aluminum as a main component, the plating layer M can be of a thick film having a thickness of 5 μm to 50 μm inclusive. In this case, through application of heat to the plating layer M, iron elements contained in stainless steel diffuses into the plating layer M, whereby the plating layer M and the outer tube member 11 are strongly joined together. Accordingly, even in the case of employment of the above-mentioned thick film, at the time of connecting and fixing the outer tube member 11 and the protective outer tube member 12 together by crimping, cracking in the plating layer M and exfoliation of the plating layer M from the outer tube member 11 can be restrained. Particularly, since the plating layer M and the outer tube member 11 are strongly joined together, even when cracking occurs, the exfoliation can be sufficiently restrained.

The plating layer M may be of a single layer or may include a first plating layer on the outer surface of the outer tube member 11 and a second plating layer formed on the outer surface of the first plating layer and differing in material from the first plating layer. If necessary, a third plating layer may be formed on the outer surface of the second plating layer. However, usually, the plating layer M composed of two plating layers of different materials can sufficiently restrain corrosion of the outer tube member 11. In the case of employment of the plating layer M composed of two plating layers, the second plating layer may be formed from a material which corrodes more easily than does the first plating layer, or a material which does not corrode easily so as to protect the first plating layer from corrosion.

Regarding an example of the plating layer M composed of two plating layers, in the case where the outer tube member 11 is formed from stainless steel, the plating layer can be such that the first plating layer contains nickel as a main component, whereas the second plating layer contains aluminum, zinc, or chromium as a main component. In a specific example of such a plating layer M, the first plating layer is a nickel plating layer, and the second plating layer is an aluminum plating layer, a zinc plating layer, or a chromium plating layer. In this case, the second plating layer corrodes more easily than does the first plating layer; thus, corrosion progresses in two stages (after the second plating layer corrodes, the first plating layer starts to corrode). Therefore, corrosion of the outer tube member 11 can be sufficiently restrained.

Nickel plating can be strongly joined to stainless steel. Therefore, when the outer tube member 11 is formed from stainless steel, through employment of a nickel plating layer as the first plating layer, the plating layer M and the outer tube member 11 can be strongly joined together. Further, as mentioned above, an aluminum plating layer or the like, which corrodes more easily than does the nickel plating layer, can be formed on the surface of the nickel plating layer. Also, in view of the fact that a plating layer of a material selected from among many materials can be formed on the surface of a nickel plating layer, preferably, the nickel plating layer is used as the first plating layer.

Regarding another example of the plating layer M composed of two plating layers, in the case where the outer tube member 11 is formed from stainless steel, the plating layer M can be such that the first plating layer contains aluminum or nickel as a main component, whereas the second plating layer contains gold as a main component. In a specific example of such a plating layer M, the first plating layer is an aluminum plating layer, and the second plating layer is a gold plating layer. Through employment of a gold plating layer, which exhibits high corrosion resistance, as the second plating layer, the outer tube member 11 can be sufficiently protected. Even when pitting corrosion or the like occurs on the gold plating layer having high corrosion resistance, the outer tube member 11 is not immediately corroded, but is sufficiently protected by means of the aluminum or nickel plating layer, which serves as the first plating layer.

No particular limitation is imposed on the thickness of the plating layer M composed of two plating layers, so long as corrosion of the outer tube member 11 is sufficiently restrained. The thickness of the plating layer M depends on a metal contained therein. When the first plating layer is a nickel plating layer, the thickness of the first plating layer is preferably 0.5 µm to 30 µm inclusive, more preferably 3 µm to 20 µm inclusive, and the total thickness of the first plating layer and the second plating layer is preferably 1 µm to 50 µm inclusive, more preferably 4 µm to 30 µm inclusive. When the first plating layer is an aluminum plating layer, the thickness of the first plating layer is preferably 0.5 µm to 30 µm inclusive, more preferably 3 µm to 20 µm inclusive, and the total thickness of the first plating layer and the second plating layer is preferably 1 µm to 50 µm inclusive, more preferably 4 µm to 30 µm inclusive. When the total thickness of the plating layer M is less than 1 µm, depending on a material used to form the plating layer M, the plating layer M may fail to yield a sufficient action or effect of restraining corrosion. When the total thickness of the plating layer M is in excess of 50 µm, at the time of connecting and fixing the outer tube member 11 and the protective outer tube member 12 together by, for example, crimping, the plating layer M may crack, resulting in exfoliation of the plating layer M from the outer surface of the outer tube member 11.

Further, in FIG. 2, the plating layer M is formed on the entire surface of the outer tube member 11. However, as shown in FIG. 3, the plating layer M may only be formed on the outer surface of the front-side separation portion R1. Also, as shown in FIG. 4, the plating layer M may only be formed on the outer surface of the front-side separation portion R1 and the outer surface of the rear-side separation portion R2. In this manner, when the plating layer M is selectively formed only on the outer surface of the front-side separation portion R1, or on the outer surface of the front-side separation portion R1 and the outer surface of the rear-side separation portion R2, the plating layer M is not formed on the seal portion A. Thus, the protection outer tube member 12 is strongly joined to the outer tube member 11, thereby preventing a rotational movement of the protective outer tube member 12.

As shown in FIG. 5, not only is the plating layer M formed on the outer tube member 11, but also may a plating layer N be formed on the protective outer tube member 12. Materials similar to those which are described above as materials for the plating layer M can be used to form the plating layer N. Formation of the plating layer N on the protective outer tube member 12 can restrain corrosion of the protective outer tube member 12. In the case where the plating layer N is formed on the protective outer tube member 12, preferably, as shown in FIG. 6, thickness t2 of the plating layer N (corresponding to the front-end metal coating layer of the present invention) formed on the front end face of the protective outer tube member 12 is greater than thickness t1 of the plating layer M formed on the outer surface of the front-side separation portion R1. By virtue of this, even though the front end face of the protective outer tube member 12 is a fracture plane, corrosion of the protective outer tube member 12 can also be prevented.

[2] Gas Sensor of a Second Embodiment

The corrosion-restraining feature of the present invention is not limited to the gas sensor 100 according to the first embodiment described above in [1], but can also be embodied in a gas sensor 200 according to a second embodiment of the present invention which differs in structure from the gas sensor 100 as shown in FIG. 7.

The gas sensor 200 includes an axially extending plate-like sensor element 101; a metallic shell 102, which holds the sensor element 101 in the interior thereof via other members; an outer tube member 111, which is fixed to a rear end portion of the metallic shell 102; and a protective outer tube member 112, which is fixedly fitted to the outer circumferential surface of a rear end portion of the outer tube member 111.

The sensor element 101 has a well-known structure such that a detecting portion 101a for detecting a component of an atmosphere to be measured, and a ceramic heater 103 are formed integral with each other. The metallic shell 102 includes a threaded portion 102a adapted to attach the gas sensor 200 to an attachment portion of an exhaust pipe, and a hexagonal portion 102b to which an attachment tool is applied in attachment to the attachment portion of the exhaust pipe. A support member 104 made of alumina is engaged with a shell-side step portion 102c of the metallic shell 102. The sensor element 101 is fixed to the support member 104 by means of a vitric seal member 104a. Further, metallic double-structured protectors 105a, 105b are welded to a front end portion of the metallic shell 102 in such a manner as to surround a front end portion of the sensor element 101 which projects from the metallic shell 102. Each of the protectors 105a, 105b has a plurality of gas intake holes. Exhaust gas flows in through the gas intake holes and undergoes detection of the concentration of oxygen contained therein.

A front end portion of the outer tube member 111 is fixedly fitted to a rear end portion of the metallic shell 102. The outer tube member 111 has an outer-tube step section 111a which is formed at a substantially center position with respect to its axial direction; a portion of the outer tube member 111 located frontward of the outer-tube step section lila serves as an outer-tube front-barrel section 111b; and a portion of the outer tube member 111 located rearward of the outer-tube step section 111a serves as an outer-tube rear-barrel section 111c. Further, the outer-tube rear-barrel section 111c has a plurality of atmosphere introduction holes 111d formed therein at predetermined circumferential intervals. A front section of the protective outer tube member 112 is coaxially fitted and connected to the outer-tube rear-barrel section 111c of the outer tube member 111. The protective outer tube member 112 also has a plurality of atmosphere introduction holes 112a formed therein at predetermined circumferential intervals. Regarding materials for the outer tube member 111 and the protective outer tube member 112, the description of the outer tube member 11 and the protective outer tube member 12 of the gas sensor 100 according to the first embodiment appearing above in [1] can be applied.

Preferably, while the protective outer tube member 112 has the atmosphere introduction holes 112a formed therein, and the outer tube member 111 has the atmosphere introduction holes 11d formed therein, a filter 106 is disposed between the protective outer tube member 112 and the outer tube member 111 at at least a position corresponding to the atmosphere introduction holes 112a, 111d. Regarding material for and other information about the filter 106, the description of the filter 8 of the gas sensor 100 according to the first embodiment appearing above in [1] can be applied.

The protective outer tube member 112 is fixed and connected to the outer tube member 111 by radially inward crimping. More specifically, the protective outer tube member 112 and the outer tube member 111 are crimped together directly at a first crimped portion S11, which is located rearward of the filter 106; the protective outer tube member 112 and the outer tube member 111 are crimped together via the filter 106 at a second crimped portion S12, which is located rearward of the atmosphere introduction holes 112a, 111d; and the protective outer tube member 112 and the outer tube member 111 are crimped together directly at a connective crimped portion S13, which is located frontward of the atmosphere introduction holes 112a, 111d. As in the case of the gas sensor 100 according to the first embodiment described above in [1], the outer tube member 111 and the protective outer tube member 112 can be fixed and connected together not only by crimping, but also by welding, such as resistance welding, laser beam welding, and electron beam welding, and press fit.

A substantially cylindrical separator 107 is disposed inside the outer-tube front-barrel section 111b of the outer tube member 111. Connection terminals 108 (only two connection terminals are shown in FIG. 9) connected to element lead wires 110a, 110b and heater lead wires 103a, 103b, respectively, are inserted into the interior of the separator 107. Meanwhile, an elastic seal member 109 made of fluorine-containing rubber or the like having excellent heat resistance is disposed inside the outer-tube rear-barrel section 111c of the outer tube member 111. The elastic seal member 109 has four lead-wire insertion holes 109a extending axially therethrough.

As shown in FIG. 8, a plating layer M is formed on the outer surface of the outer tube member 111 including the outer surface of a front-side separation portion R11 and the outer surface of a rear-side separation portion R12. Regarding material for and other information about the plating layer M, the previously given description of the plating layer M of the gas sensor 100 according to the first embodiment can be applied. By virtue of the plating layer M formed on the outer surface of the front-side separation portion R11, even when salt water or the like stagnates in a clearance B11 between the inner surface of the protective outer tube member 112 and the outer surface of the front-side separation portion R11, corrosion of the outer tube member 111 can be restrained, thereby preventing deterioration in detection accuracy of the sensor.

Also, by virtue of the plating layer M formed on the outer surface of the rear-side separation portion R12, even when salt water or the like stagnates in a clearance B12 between the inner surface of the protective outer tube member 112 and the outer surface of the rear-side separation portion R12, corrosion of the outer tube member 111 can be restrained, thereby preventing deterioration in detection accuracy of the sensor.

Preferably, the plating layer M is not formed on a joint portion 115 between the outer tube member 111 and the metallic shell 102. By virtue of this, the outer tube member 111 can be strongly joined to the metallic shell 102, thereby preventing dropping-off of the outer tube member 111 from the metallic shell 102.

Further, in FIG. 8, the plating layer M is formed on the entire outer surface of the outer tube member 111 except for the outer surface of the joint portion 115 between the outer tube member 111 and the metallic shell 102. However, as shown in FIG. 9, the plating layer M may only be formed on the outer surface of the front-side separation portion R11 and the outer surface of the rear-side separation portion R12. Also, as shown in FIG. 9, the plating layer M may extend up to the outer surface of a facing portion R13 which is provided at the step section 111a of the outer tube member 111 and which faces the protective outer tube member 112. A clearance B13 is formed between the step section 111a of the outer tube member 111 and the front end of the protective outer tube member 112; accordingly, salt water or the like may stagnate in the clearance B13. However, by means of the metal coating layer M extending up to the outer surface of the facing portion R13 as mentioned above, there can be restrained corrosion of the outer tube member, which could otherwise result from salt water which stagnates in the clearance B13 between the step section 111a and the protective outer tube member 112.

As mentioned above, when the plating layer M is selectively formed only on the outer surface of the front-side separation portion R11, or on the outer surface of the front-side separation portion R11 and the outer surface of the rear-side separation portion R12, the plating layer M is not formed on the seal portion A. Thus, the protection outer tube member 112 is strongly joined to the outer tube member 111, thereby preventing a rotational movement of the protective outer tube member 112.

As shown in FIG. 10, not only is the plating layer M formed on the outer tube member 111, but also may a plating layer N similar to the plating layer M be formed on the protective outer tube member 112. By virtue of this, corrosion of the protective outer tube member can be restrained.

BRIEF DESCRIPTION OF THE DRAWINGS

[FIG. 1] Schematic sectional view of a gas sensor according to a first embodiment of the present invention.

[FIG. 2] Fragmentary enlarged view of a portion of the gas sensor of FIG. 1 at which an outer tube member and a protective outer tube member are fixed and connected together through crimping, showing a state where a plating layer is formed on the entire surface of the outer tube member.

[FIG. 3] Fragmentary enlarged view showing a state where the plating layer is only formed on the outer surface of a front-side separation portion of the outer tube member in the fragmentary enlarged view of FIG. 2.

[FIG. 4] Fragmentary enlarged view showing a state where the plating layer is only formed on the outer surface of the front-side separation portion and the outer surface of a rear-side separation portion of the outer tube member in the fragmentary enlarged view of FIG. 2.

[FIG. 5] Fragmentary enlarged view showing a state where the plating layer is formed on the entire surface of the outer tube member and the entire surface of the protective outer tube member in the fragmentary enlarged view of FIG. 2.

[FIG. 6] Fragmentary enlarged view showing a state where a front-end metal coating layer thicker than a metal coating layer formed on the outer tube member is formed on the front end of the protective outer tube member.

[FIG. 7] Schematic sectional view of a gas sensor 200 according to a second embodiment of the present invention.

[FIG. 8] Fragmentary enlarged view of a portion of the gas sensor of FIG. 7 at which an outer tube member and a protective outer tube member are fixed and connected together through crimping, and a joint portion of the gas sensor of FIG. 7 at which the outer tube member and a metallic shell are joined together, showing a state where a plating layer is formed on the entire outer surface of the outer tube member except for the outer surface of the joint portion between the outer tube member and the metallic shell.

[FIG. 9] Fragmentary enlarged view of a portion of the gas sensor of FIG. 7 at which the outer tube member and the protective outer tube member are fixed and connected together through crimping, showing a state where the plating layer is formed on the outer surface of a front-side separation portion, the outer surface of a rear-side separation portion, and the outer surface of a facing portion R13 of the outer tube member.

[FIG. 10] Fragmentary enlarged view of a portion of the gas sensor of FIG. 7 at which the outer tube member and the protective outer tube member are fixed and connected together through crimping, showing a state where the plating layer is formed on the entire surface of the outer tube member and the entire surface of the protective outer tube member.

[FIG. 11] Fragmentary enlarged view showing a crack generated in the outer tube member in a boundary region between a front-side separation portion and a seal portion of a connective crimped portion, at which the outer tube member and the protective outer tube member are fixed and connected together as shown in FIG. 2.

[FIG. 12] Fragmentary enlarged view showing a crack generated in the outer tube member in a boundary region between a rear-side separation portion and a seal portion between the outer tube member and the protective tube member located frontward of a third crimped portion in the fragmentary enlarged view of FIG. 2.

DESCRIPTION OF REFERENCE NUMERALS 100, 200: gas sensor; 11, 111: outer tube member; 12, 112: protective outer tube member; 2, 101: sensor element; 4, 102: metallic shell; 6, 107: separator; 8, 106: filter; S4, S13: connective crimped portion; A: seal portion; R1, R11: front-side separation portion; R2, R12: rear-side separation portion; R13: facing portion; M, N: plating layer

The invention claimed is:

1. A sensor comprising:
a sensor element which extends axially and whose front end portion is exposed to a gas to be measured;
a metallic shell surrounding the sensor element;
an outer tube member fixed to a rear end portion of the metallic shell; and
a protective outer tube member covering an outer surface of the outer tube member;
the outer tube member having a seal portion being circumferentially in contact with the protective outer tube member directly or via another member, and a front-side separation portion located frontward of the seal portion and spaced apart from and facing the protective outer tube member;
wherein a metal coating layer is formed on an outer surface of at least the front-side separation portion of the outer tube member.

2. A sensor according to claim 1, wherein at least a portion of an outer surface of the seal portion is exposed from the metal coating layer.

3. A sensor according to claim 1, wherein the outer tube member has a joint portion joined to the metallic shell, and
at least a portion of an outer surface of the joint portion is exposed from the metal coating layer.

4. A sensor according to claim 1, wherein the metal coating layer is formed from a material which corrodes more easily than does the outer tube member.

5. A sensor according to claim 1, wherein the outer tube member is formed from a stainless steel, and the metal coating layer is formed from a metal which contains aluminum, zinc, chromium, or nickel as a main component.

6. A sensor according to claim 1, wherein the metal coating layer has a thickness of 1 μm to 50 μm inclusive.

7. A sensor according to claim 1, wherein the outer tube member is formed from a stainless steel; the metal coating layer contains aluminum as a main component; and the metal coating layer has a thickness 5 μm to 50 μm inclusive.

8. A sensor according to claim 1, wherein the outer tube member is formed from an austenitic stainless steel.

9. A sensor according to claim 1, wherein the protective outer tube member has at least one atmosphere introduction hole for introducing the atmosphere into the interior of the protective outer tube member, and the outer tube member has at least one atmosphere introduction hole for introducing the atmosphere into the interior of the outer tube member;
a filter is disposed between the atmosphere introduction hole of the protective outer tube member and the atmosphere introduction hole of the outer tube member, and the seal portion is formed frontward of the filter; and
the outer tube member has a rear-side separation portion located rearward of the seal portion and frontward of the filter and spaced apart from and facing the protective outer tube member, and the metal coating layer formed on an outer surface of at least the rear-side separation portion of the outer tube member.

10. A sensor according to claim 1, wherein the protective outer tube member has a front-end metal coating layer formed on a front end face of the protective outer tube member, and
the front-end metal coating layer is greater in thickness than the metal coating layer.

11. A sensor according to claim 1, wherein the outer tube member has a rear section surrounded by the protective outer tube member and having the seal portion and the front-side separation portion, a front section greater in diameter than the rear section, and a step section connecting the rear section and the front section;

the step section has a facing portion which faces the protective outer tube member; and the metal coating layer is formed on an outer surface of the outer tube member which extends from the front-side separation portion to at least the facing portion.

12. A sensor according to claim 1, wherein the metal coating layer includes a first metal coating layer formed on the outer surface of the outer tube member, and a second metal coating layer formed on an outer surface of the first metal coating layer and differing in composition from the first metal coating layer.

13. A sensor according to claim 12, wherein the outer tube member is formed from a stainless steel; the first metal coating layer contains nickel as a main component; and the second metal coating layer contains aluminum, zinc, or chromium as a main component.

14. A sensor according to claim 12, wherein the outer tube member is formed from a stainless steel; the first metal coating layer contains aluminum or nickel as a main component; and the second metal coating layer contains gold as a main component.

* * * * *